United States Patent [19]
Schulte-Elte et al.

[11] Patent Number: 6,054,426
[45] Date of Patent: Apr. 25, 2000

[54] OPTICALLY ACTIVE ALIPHATIC ALCOHOLS AND THEIR USE AS PERFUMING INGREDIENTS

[75] Inventors: Karl-Heinrich Schulte-Elte, Onex; Christian Margot, Bassins; Christian Chapuis, Mies, all of Switzerland; Dana Philip Simmons, Jamestown, N.C.; Daniel Reichlin, Confignon, Switzerland

[73] Assignee: Firmenich SA, Geneva, Switzerland

[21] Appl. No.: 08/218,543

[22] Filed: Mar. 28, 1994

Related U.S. Application Data

[63] Continuation-in-part of application No. 07/695,479, May 3, 1991, abandoned.

[30] Foreign Application Priority Data

May 16, 1990 [CH] Switzerland .............................. 1671/90

[51] Int. Cl.$^7$ .................................................. A61K 7/46
[52] U.S. Cl. ............................................. 512/22; 568/822
[58] Field of Search ............................... 568/822; 512/22

[56] References Cited

U.S. PATENT DOCUMENTS

| | | | |
|---|---|---|---|
| 4,626,602 | 12/1986 | Schulte-Elte et al. | 568/822 |
| 4,800,233 | 1/1989 | Simmons | 568/447 |
| 5,250,512 | 10/1993 | Ohmoto et al. | 512/22 |

FOREIGN PATENT DOCUMENTS

| | | | |
|---|---|---|---|
| 118809 | 9/1984 | European Pat. Off. | 512/22 |
| 121828 | 10/1984 | European Pat. Off. | 512/22 |

OTHER PUBLICATIONS

Helv. Chim. Acta, 68, 1961–1985 (1985).
Brunke et al., "Uber Chemische Struktur und Geruckseffekt in der Tetrahydrojonal–Reihe," pp. 199–203.
Theilheimer, "Synthetic Methods of Organic Chemistry," vol. 9, p. 59 and vol. 15, pp. 83–84.

*Primary Examiner*—James H. Reamer
*Attorney, Agent, or Firm*—Pennie & Edmonds LLP

[57] ABSTRACT

The optically active compounds of formula

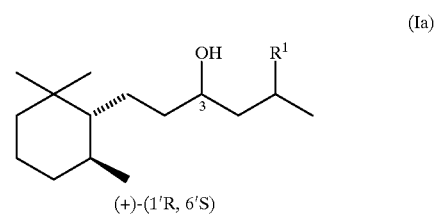

(Ia)

(+)-(1'R, 6'S)

wherein $R^1$ represents a hydrogen atom or a methyl radical, or of formula

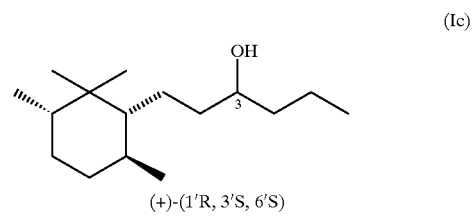

(Ic)

(+)-(1'R, 3'S, 6'S)

are useful as perfuming ingredients for the preparation of perfuming compositions and perfumed articles to which they impart woody-amber notes.

21 Claims, No Drawings

OPTICALLY ACTIVE ALIPHATIC ALCOHOLS AND THEIR USE AS PERFUMING INGREDIENTS

This is a continuation in part of application Ser. No. 695,479, filed on May 3, 1991, now abandoned.

BACKGROUND AND BRIEF DESCRIPTION OF THE INVENTION

The present invention relates to the perfume industry. It concerns, more particularly, novel optically active isomers of two aliphatic alcohols represented by the formula

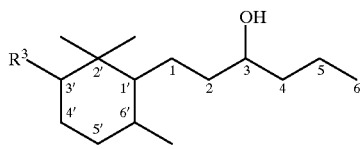

wherein symbol $R^3$ stands for a hydrogen atom or a methyl radical, i.e. 1-(2',2',6'-trimethyl-1'-cyclohexyl)-3-hexanol and 1-(2',2',3',6'-tetramethyl-1'-cyclohexyl)-3-hexanol.

Both the alcohols of formula (I) above and their racemic stereoisomers are known compounds. For example, U.S. Pat. No. 4,623,750, belonging to the present applicant, discloses the cis- and trans-configuration isomers of 1-(2',2',6'-trimethyl-1'-cyclohexyl)-3-hexanol having the structures

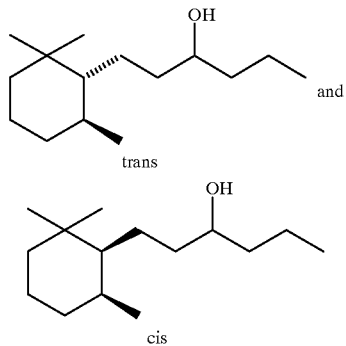

According to this prior art reference, the trans isomer, and the mixtures rich in said isomer, present a more pronounced animal and ambery odor character than the cis isomer.

The two prior known compounds are racemic species, i.e. each of them is a mixture of four optically active isomers. There is absolutely no mention of the latter in U.S. Pat. No. 4,623,750, nor of any eventually useful properties thereof.

On the other hand, U.S. Pat. No. 4,626,602, which also belongs to the present applicant, discloses, amongst others, 1-(2',2',3',6'-tetramethyl-1'-cyclohexyl)-3-hexanol and its configuration isomers, as well as their use in perfumery. This patent discloses in particular that the trans-configuration isomers of formula

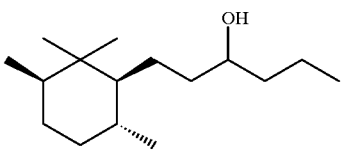

i.e. those possessing the three substituents of the six-membered ring (positions 1', 3' and 6') in equatorial position, are judged to be distinctly superior to their cis-configuration homologues, as regards the olfactive qualities, which are said to be distinct from one configuration isomer to the next. Once again, this document mentions only racemic forms of the stereoisomers, in spite of the fact that these alcohols possess several chiral centers and their racemates are therefore mixtures of a plurality of optically active species. There is no citation in the prior art as to whether these optically active isomers could themselves be useful perfuming ingredients.

One of the aims of the man skilled in the art of perfumery is to find new chemicals which are more performant than prior known compounds from an olfactive point of view, either because their odor qualities are more distinctive and original or because their odor is much stronger or yet, if he is lucky, as a result of both of these. Such a skilled man knows well enough that he cannot rely on structural closeness to predict whether a new chemical will be a more interesting fragrance ingredient or, even, whether it will be fragrant at all. Although he cannot be unaware of the role that the optical isomerism of a compound plays in determining its odor properties or, rather, its odor perception by the perfumer [see, for instance, W. Pickenhagen, in ACS Symposium Series 388, chapter 12, p. 151, ed. ACS, Washington DC (1989)], he often finds no motivation to prepare the optically active isomers, particularly when confronted with racemic compounds which possess a plurality of chiral centers, knowing that his task will be extremely difficult and unobvious, as the synthesis of the corresponding pure optical isomers not only requires particular expertise but is also costly. In addition, he may find no reward, as there is no way of predicting, even in the presence of a good racemate, whether his efforts will lead only to the discovery that none of the pure optically active components of said racemate is in any way superior to the latter, as a fragrance ingredient or, at least, not superior enough to justify its inevitably dearer industrial development.

In spite of such difficulties, the synthesis of novel chiral perfuming ingredients is an ever increasing need in this industry. The reason for this springs in an obvious manner from articles such as that of G. Ohloff in Experientia 42, 271 (1986), wherein the author not only impresses upon its reader the importance of every new discovery of fragrant chemicals towards completing an empirically set list of structural conditions or parameters, amongst which chiral activity, disclosed in this article and believed to influence odor perception, but also acknowledges the transient quality, at the present stage of the art, of such lists of structural parameters which, as he admits, every new compound behaving uncharacteristically may well contradict, leading to replacements or alterations (see, for example, the conclusion on page 277). Yet, despite the necessity to continue preparing optically active species of known racemates, the outcome of such an endeavour is rendered all the more uncertain and unobvious by the fact that a racemate does not generally produce a fragrance effect which corresponds to a sum of the individual odor properties of the different optically active isomers present in the racemic mixture, both qualitatively and quantitatively, and this even when there are only two of such isomers in said mixture. The olfactive properties of the racemate can be, and often are, quite different from those of each optically active component of said racemate and, that is why it is impossible to predict the olfactive behaviour of any one isomer on the basis of the knowledge of the racemate, particularly when, as is the case here, there are several optically active isomers in the racemic mixture. The result of the chemist's research in this domain is therefore unpredictable.

It should be further noted that in the present case, the individual optically active isomers cannot be simply separated from the known racemic mixtures, but require specifically designed and sophisticated syntheses, as described further on.

The present invention is yet another example of this reality and it brings precisely a new and unexpected contribution into this field.

PREFERRED EMBODIMENTS OF THE INVENTION

We have now discovered with surprise that the odor properties, in particular the olfactive strength, which up until now had been associated with the trans-configuration isomers of alcohols (I) mentioned above, in their racemic form, are not in fact inherent to all the optically active components of the racemates. Quite the contrary, each one of the novel optically active isomers which are the object of the present invention possesses a specific odor, quite distinct from that of the others, and the intensity of which can vary in a wide range of values. In addition, some of said optically active isomers are distinctly advantageous, as regards perfumery applications, when compared to their racemic mixture counterparts known from the prior art.

One aim of the present invention is to provide an optically active compound of formula

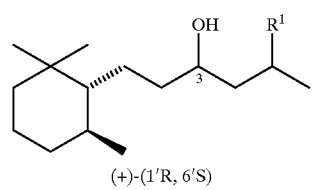

(Ia)

(+)-(1'R, 6'S)

wherein $R^1$ represents a hydrogen atom or a methyl radical, or of formula

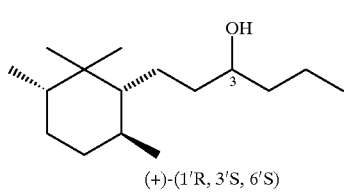

(Ic)

(+)-(1'R, 3'S, 6'S)

Compounds of formulae (Ia) and (Ic) both possess woody odor notes, the character and strength of which vary nonetheless from one compound to the other, and are also distinct from those of the respective antipodes. For example, the mixture of C(3) epimers represented by formula (Ic), or (+)-(1'R,3'S,6'S)-1-(2',2',3',6'-tetramethyl-1'-cyclohexyl)-3-hexanol, a preferred compound of the invention, possesses a woody-amber odor of extraordinary intensity, together with a slight transpiration side note. As a result of its olfactive character and far stronger note than that of racemic 1-(2', 2',c-3',t-6'-tetramethyl-r-1'-cyclohexyl)-3-hexanol described in U.S. Pat. No. 4,626,602, the above-mentioned optically active compound compares advantageously with the prior art racemate in the applications according to the invention, as it is shown in the related comparative example presented further on. As to its antipode, the mixture of C(3) epimers of formula

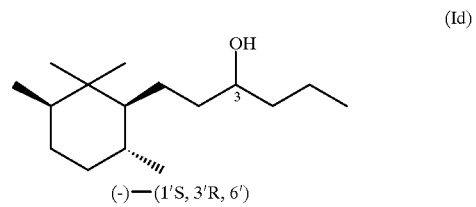

(Id)

(-)—(1'S, 3'R, 6')

or (-)-(1'S,3'R,6'R)-1-(2',2',3',6'-tetramethyl-1'-cyclohexyl)-3-hexanol, it develops a much weaker odor, albeit of similar character.

The optically active mixture of C(3) epimers of formula (Ia), wherein R is hydrogen, possesses a woody odor note which is more elegant and less animal than those of its homologues methylated in position 3' of the ring, cited above, which is also weaker and less dry than the odors of the latter. The compound of formula (Ia) has also been judged superior, from an olfactive point of view, to its antipode of formula

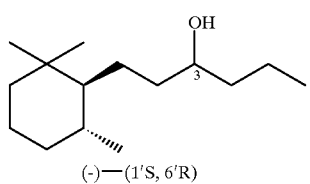

(Ib)

(-)—(1'S, 6'R)

In addition, a great variety of olfactive intensities has been observed amongst the four optically active isomers of formula

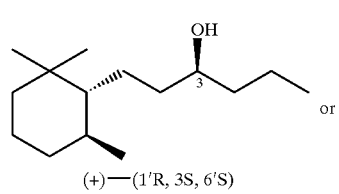

(IIa)

(+)—(1'R, 3S, 6'S)

or

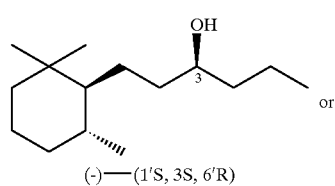

(IIb)

(-)—(1'S, 3S, 6'R)

or

-continued

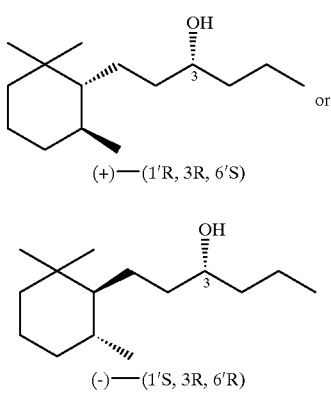

all with a trans-configuration and all present in the prior known racemic mixture. Thus, (+)-(1'R,3S,6'S)-1-(2',2',6'-trimethyl-1'-cydohexyl)-3-hexanol (IIa) turns out to be the prime quality compound of the series, the odor note of which is far stronger and tenacious than that of the other isomers. This compound possesses in fact a very elegant woody-amber note, which compares advantageously with that of trans-1-(2',2',6'-trimethyl-1'-cyclohexyl)-3-hexanol, the mixture of the four isomers cited which is described in U.S. Pat. No. 4,623,750 without, however, replacing it. The odor of this optically active isomer is stronger and more tenacious than that of the racemate, while possessing a still more pronounced woody character.

The compound of formula (IIb), or (−)-(1'S,3S,6'R)-1-(2',2',6'-trimethyl-1'-cyclohexyl)-3-hexanol, develops an odor of similar character of that of compound (IIa) above, the intensity of which is already much weaker. As for the C(3) epimers of these two compounds, represented by formulae (IIc) and (IId), their odor notes are practically devoid of animal character and their olfactive strength is uncharacteristically weak, far weaker than that of preferred compound (IIa).

On the other hand, the optically active mixtures of C(3) epimers of formula (Ia), wherein $R^1$ represents a methyl radical, are also characterized by woody notes resembling those of their unsubstituted homologues (in position 5 of the chain). The odor note of (+)-(1'R,6'S)-5-methyl-1-(2',2',6'-trimethyl-1'-cyclohexyl)-3-hexanol, represented by the formula

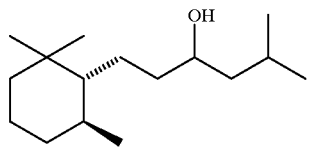

is far stronger than that of its enantiomer (−)-(1'S,6'R)-5-methyl-1-(2',2',6'-trimethyl-1'-cyclohexyl)-3-hexanol.

When comparing between themselves the odor properties of the preferred compounds of the invention, i.e. (+)-(1'R, 3'S,6'S)-1-(2',2',3',6'-tetramethyl-1'-cyclohexyl)-3-hexanol and (+)-(1'R,3S,6'S)-1-(2',2',6'-trimethyl-1'-cyclohexyl)-3-hexanol, it becomes evident that their use for the preparation of perfuming compositions and perfumed articles is as much a function of the desired fragrant effect as it is dependent on the taste of the perfumer. In fact, while the latter mentioned compound is judged of an easier application as a result of its weaker odor, whose effect does not overwhelm the composition, and it is also preferred when a more elegant perfuming effect is desired, the more aggressive and animal note of (+)-(1'R,3'S,6'S)-1-(2',2',3',6'-tetramethyl-1'-cyclohexyl)-3-hexanol is just as appreciated by the perfumers when used in masculine type perfuming compositions.

The compounds of the invention can be widely used, either by direct incorporation into the products to be perfumed or, as is more current, in admixture with other perfuming ingredients and the usual solvents or adjuvants.

The concentrations in which these compounds can be added to the perfuming compositions into which they are incorporated are obviously a function of the desired fragrance effect and of the nature of the other perfuming coingredients, as well as of the odor intensity of the particular compound according to the invention. By way of example, concentrations of the order of 5 to 10%, or even 20% by weight, may be cited but the application examples presented further on show that far lower values of concentration may be used, particularly when applying the preferred (+)-(1'R,3S,6'S)-1-(2',2',6'-trimethyl-1'-cyclohexyl)-3-hexanol or (+)-(1'R,3'S,6'S)-1-(2',2',3',6'-tetramethyl-1'-cyclohexyl)-3-hexanol, the latter of these being used in yet weaker concentrations than the former.

The compounds of the invention can also be conveniently used to perfume varied articles such as soaps, bath or shower gels, shampoos, hair conditioners, body deodorizers, cosmetic preparations, air fresheners, detergents or fabric softeners, or household products.

According to the invention, an optically active mixture of C(3) epimers of formula (Ia) to (Id), or their homologues methylated in the chain, can be prepared following an original process, which comprises reducing a ketone in the form of an optically active enantiomer of formula

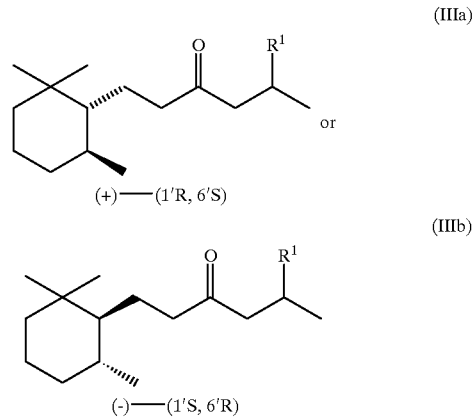

wherein symbol $R^1$ stands for a hydrogen atom or a methyl radical, or, respectively, of formula

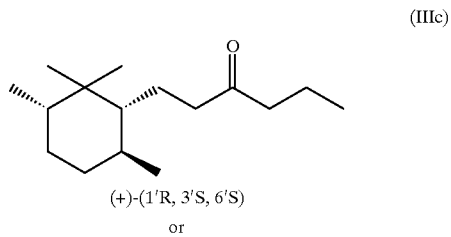

-continued

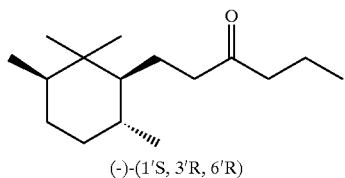

(IIId)

(-)-(1'S, 3'R, 6'R)

by means of an alkali metal aluminum hydride, to give a mixture of epimers of formula (Ia) or (Ib) or, respectively, a mixture of epimers of formula (Ic) or (Id).

The ketones of formulae (IIIa) to (IIId), used as starting products in the process according to the invention, can be obtained by aldol condensation with 2-pentanone or 4-methyl-2pentanone of an aldehyde, in the form of an appropriate optically active isomer, followed by hydrogenation, as represented in the following reaction scheme:

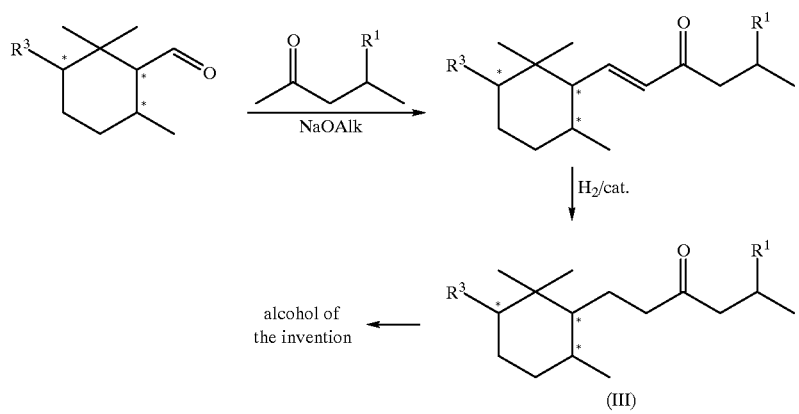

$R^1 = H$ and $R^3 = CH_3$; or
$R^1 = H, CH_3$ and $R^3 = H$
Alk = $CH_3, CH_2H_5$
* = chiral center The specific reaction conditions are described in detail in the preparation examples.

The starting optically active aldehydes of formula

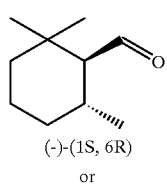

(-)-(1S, 6R)

or

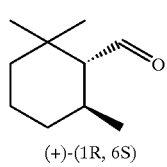

(+)-(1R, 6S)

can be prepared from optically active citronellal, following the process described in U.S. Pat. No. 4,800,233.

On the other hand, the aldehydes of formula

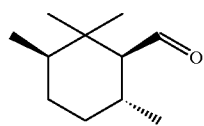

(-)-(1S, 3R, 6R)

or

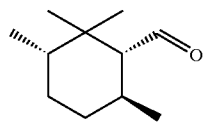

(+)-(1R, 3S, 6S)

can be prepared following the method described in published European patent application n° 374 509, the content of which is here included by reference. The specific preparation conditions are described in detail in the examples presented further on.

The reduction of the ketone of formulae (IIIa) to (IIId) is carried out conventionally by means of $LiAlH_4$ for example, and the specific conditions of such reactions are also described in the examples.

We have otherwise discovered that when it was desired to prepare a compound of formulae (IIa) to (IId), or the corresponding methylated homologues, according to the invention, it was more convenient to follow another method which is also the object of the present invention. This is a process which comprises reacting a hydroxy-sulfone of formula

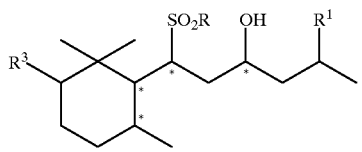

(IV)

wherein the asterisk indicates the location of a chiral center, symbol R stands for an alkyl or aryl radical and symbols $R^1$ and $R^3$ are defined as in formula (I), in the form of an appropriate optically active isomer, with an agent capable of the reductive cleavage of the sulfonyl group and subsequently separating the desired epimer from the reaction product.

It is described in the prior art that the cleavage of a C—S bond can be obtained by means of an alkali metal, namely lithium. For example, C.G. Screttas et al., in J. Org. Chem. 43, 1064 (1978) described the cleavage reactions of alkyl phenyl sulfides by means of lithium dispersions, in the presence of a catalytic amount of naphthalene, in THF (tetrahydrofuran). Other reaction conditions have been disclosed by R. J. Armstrong et al., in Can. J. Chem. 61, 2530 (1983) (and references therein). These authors described the hydrogenolysis of a hydroxy-sulfone by means of a 6% Na—Hg alloy.

According to a preferred embodiment of the process of the present invention, an appropriate optically active isomer of the hydroxy-sulfone of formula (IV), wherein symbol R represents a phenyl radical, is reacted with lithium naphthalide, in tetrahydrofuran. The reaction is regiospecific and the optically active isomer of formulae (IIa) to (IId) which corresponds to the starting optically active isomer of hydroxy-sulfone (IV) is obtained as a final product, together with minor amounts of its unsaturated chain homologue of formula

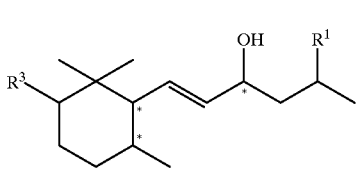

(V)

* = chiral center
$R^1$, $R^3$ = defined as in formula (I)

This allylic alcohol can then be separated from the mixture by acetylation of the latter, followed by ozonolysis, reduction and chromatographic separation, as described in the preparation examples presented further on. This treatment provides the desired compound of formula (IIa), (IIb), (IIc) or (IId), or homologues, in a pure state.

In addition to this preferred embodiment, other reaction conditions have also been studied, for example, the reduction of the phenyl-sulfonyl group by means of a lithium suspension in ethylamine, or yet of a 6% Na—Hg alloy under the conditions described in the prior art. These two methods are also quite convenient for preparing the compounds according to the invention. They are however less efficient than the preferred embodiment, as a result of the fact that they yield mixtures which are richer in side product (V).

The optically active hydroxy-sulfones of formula (IV), the optical purity of which determines that of the final product, can be obtained according to the process represented in the following scheme for a particular optically active isomer.

Scheme II

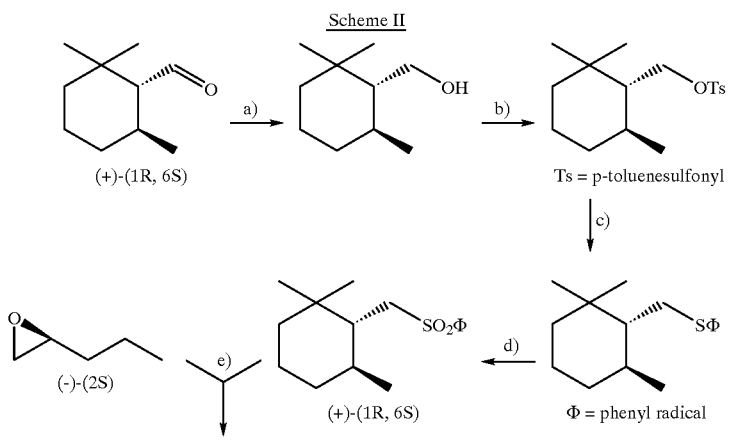

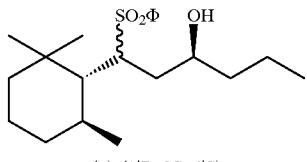

(+)-(1'R, 3S, 6'S)

a) NaBH₄
b) p-Toluenesulfonyl chloride/pyridine
c) C₆H₅SH/K/EtOH
d) m-Chloroperoxybenzoic acid (MCPBA)
e) n-Butyllihium/THF The first step in this process is a reduction of the appropriate enantiomer of trans-2,2,6-trimethyl-1-cyclohexanecarbaldehyde into the corresponding alcohol. The latter is then converted, in three steps, into a sulfone, in an analogous manner to that described by R. J. Armstrong & al. in the above-cited reference.

In order to guaranty the optical purity of the desired final product, the sulfones thus obtained were repeatedly recrystallized from ethanol, until a constant value of the corresponding optical rotation angle was obtained. The spectroscopic analysis of these sulfones [NMR, using a chiral shift reagent, i.e. Eu(HFBC)₃, HFBC=3-(heptafluorobutyryl)-d-camphorato] showed that their optical purity was above 99%.

Likewise, a similar degree of optical purity for the two 2-propyloxirane enantiomers, prepared from either D- or L-norvaline according to a known process [see, for example, B. Koppenholfer et al., Synthesis 1982, 316], was ensured by repeated recrystallizations of intermediate products. The spectroscopic analysis, under the conditions mentioned above, of (+)-(2R)-2-propyloxirane and (−)-(2S)-2-propyloxirane showed an optical purity above 99% in both cases.

The last step of the process illustrated in scheme II is a regioselective coupling of one or the other optically pure isomer of said sulfone, i.e. (+)-(1R,6S) or (−)-(1S,6R), previously deprotonated by means of n-butyl lithium in THF, with one of the other of the above-mentioned pure optically active isomers of 2-propyloxirane. This reaction provides the four pure optically active trans isomers of hydroxy-sulfone, of which only one is represented in scheme II (the isomerism of the SO₂Φ group has not been considered).

The above-described process for the preparation of compounds of formula (IIa) to (IId) according to the invention can be used analogously to prepare C(3) epimers of the formula (Ic) or (Id) compounds. One has to use then, as a starting product in the process of scheme II, an appropriate optically active isomer of 2,2,c-3,t-6-tetramethyl-r-1-cyclohexanecarbaldehyde. As it has been previously mentioned, this isomer can be obtained as described in published European patent application n° 374 509.

On the other hand, the methylated chain homologues of compounds (IIa) to (IId) can be obtained as shown in Scheme II by replacing, in the last step of the process, 2-propyloxirane by 2-(2'-méthylpropyl)oxirane, which can be prepared from D- or L-leucine.

The invention will now be described in a more detailed manner, by way of the following preparation examples, wherein the temperatures are given in degrees centigrade and the abbreviations have the usual meaning in the art. The invention will also be illustrated by examples of perfumery applications.

EXAMPLE 1

Preparation of (+)-(1'R,3'S,6'S)-1-(2',2',3',6'-tetramethyl-1'-cyclohexyl)-3-hexanol a) (+)-(1'R,3'S,6'S)-1-(2',2',3',6'-tetramethyl-1'-cyclohexyl)-3-hexanone A reactor under nitrogen was charged with 15.3 g (91.07 mmol) of (+)-(3S,5S,8S)-4,4,5,8-tetramethyl-1-oxaspiro [2.5]octane ([α]$^D_{20}$=+36.00°; prepared as described in European patent application n° 374 509) in 200 ml of toluene, in the presence of 2 ml of BF₃ etherate, and the mixture was stirred at room temperature for 15 min. The reaction mixture was poured on ice, extracted with ether, washed to neutrality with aqueous NaCl, dried over Na₂SO₄, filtered and concentrated. Around 15.3 g of a raw product, identified by gas chromatography as (+)-(1R,3S,6S)-2,2,3,6tetramethyl-1-cyclohexanecarbaldehyde, were obtained and this product was used as such in the following reactions ([α]$^D_{20}$=+7.4°, c=2.5% CHCl₃).

A 3-neck flask equipped with a condenser, a thermometer and an introduction funnel, maintained under nitrogen, was charged with 2.30 g (0.100 at. g) of Na in 35 ml of ethanol (dry) and the mixture was stirred until complete formation of the ethylate. It was then cooled to 0° with an icy bath and a solution of 15.3 g (91 mmol) of the above-mentioned aldehyde and 23.2 g (0.270 mol) of 2-pentanone was introduced dropwise. The reaction mixture was stirred overnight at room temperature, poured on ice, washed to neutrality, dried over Na₂SO₄, filtered and concentrated. After bulb-to-bulb distillation, 3.6 g (yield: 17% from the epoxyde) of pure (+)-(1'R,3'S,6'S)-1-(2',2',3',6'-tetramethyl-1'-cyclohexyl)-1-hexen-3-one ([α]$^D_{20}$=+19.0°) were obtained.

A 1-neck flask equipped with a hydrogenation head was charged with 3.35 g (14.19 mmol) of the none prepared above, 35 ml of cyclohexane, 500 mg of 5% Pd/C and the mixture was hydrogenated for 1 night (volume of H₂ consumed=210 ml) at room temperature. After filtering on Celite® and concentrating, 3.8 g of raw product were obtained. Bulb-to-bulb distillation (0.05×10² Pa) of the latter provided 3.0 g of pure (+)-(1'R,3'S,6'S)-1-(2',2',3',6'-tetramethyl-1'-cyclohexyl)-3-hexanone (yield. 89%).

[α]$^D_{20}$=+8.8°

The analytical data of this product were identical to the values published by K. H. Schulte-Elte et al. relative to the racemic hexanone, or 1-(2,2,c-3,t-6-tetramethyl-r-1-cyclohexyl)-3-hexanone, in Helv. Chim. Acta 68, 1976 (1985).

b) A 4-neck flask equipped with a magnetic stirrer was charged with 10 ml of absolute sulfuric ether and 0.15 g (3.15 mmole) of LiAlH₄. A solution of 1.0 g (4.2 mmol) of the ketone prepared according to a) in 10 ml of ether was added dropwise. The mixture was stirred for 1 night at room temperature. The reaction product was hydrolyzed by means of 0.15 ml of water, 0.15 ml of 4N NaOH and 0.45 ml of water. After filtering on Celite® and concentrating, 1.3 g of raw product were obtained. Bulb-to-bulb distillation of the latter (0.05×10² Pa) provided 0.9 g (yield. 90%) of pure (+)-(1'R,3'S,6'S)-1-(2',2',3',6'-tetramethyl-1'-cyclohexyl)-3-hexanol.

$[α]^D_{20}$=+10.6°

The analytical data of the compound were identical to those of 1-(2,2,c-3,t-6-tetramethyl-r-1-cyclohexyl)-3-hexanol published in the reference cited in a). The optical purity (>98%) of the starting ketone of formula (IIId) was confirmed by NMR in the presence of Eu(HFBC)₃.

EXAMPLE 2

Preparation of (−)-(1'S,3'R,6'R)-1-(2',2',3',6'-tetramethyl-1'-cyclohexyl)-3-hexanol This compound was prepared in an analogous way to that described in Example 1, but starting from 11.3 g (66.66 mmol) of (−)-(3R,5R,8R)-4,4,5,8-tétraméthyl-1-oxaspiro[2.5]octane ($[α]^D_{20}$=−35.1°; prepared as described in European patent application n° 374 509).

3.4 g of (−)-(1'S,3'R,6'R)-1-(2',2',3',6'-tetramethyl-1'-cyclohexyl)-1-hexen-3-one: $[α]^D_{20}$=−23.0° were obtained.

Hydrogenation of 3.3 g of this none provided 3.2 g of pure (−)-(1'S,3'R, 6'R)-1-(2',2',3',6'-tetramethyl-1'-cyclohexyl)-3-hexanone: $[α]^D_{20}$=−8.6°.

Treatment of 3.2 g of this hexanone, according to the method described in Example 1b), provided 2.8 g of pure (−)-(1'S,3'R,6'R)-1-(2',2',3',6'-tetramethyl-1'-cyclohexyl)-3-hexanol: $[α]^D_{20}$=−10.4°.

The optical purity (>98%) of the starting ketone of formula (IIIc) was confirmed by NMR in the presence of Eu(HFBC)₃.

EXAMPLE 3

Preparation of (+)-(1'R3S6'S)-1-(2',2',6'-trimethyl-1'-cyclohexyl)-3-hexanol a) (+)-(1R,6S) phenyl (2,2,6-trimethyl-1-cyclohexyl)methyl sulfone Into a reactor containing 5.0 g (0.13 mol) of NaBH₄ in 150 ml of ethanol there were added 19.2 g (0.10 mol, 83% pure) of (+)-(1R,6S)-2,2,6-trimethyl-1-cyclohexanecarbaldehyde ($[α]^D_{25}$=+0.68°; mixture 1R:1S=8:1; prepared according to the process described in U.S. Pat. No. 4,800,233). After 3 h stirring, the reaction mixture was poured on water and extracted with petroleum ether (30–60°). The combined extracts were dried over Na₂SO₄ at reduced pressure. The raw alcohol thus obtained, 20.3 g, was dissolved in 200 ml of pyridine and 27.4 g (0.14 mol) of p-toluenesulfonyl chloride were added thereto in 5 portions. After stirring overnight, the mixture was poured on cold water and extracted with ether. The combined extracts were washed with a 10% HCl aqueous solution, a NaHCO₃ aqueous solution and aqueous NaCl. The product was dried over Na₂SO₄ and concentrated at reduced pressure. The raw tosylate thus obtained, 29 g, was dissolved in 50 ml of ethanol and added dropwise to a solution of 7.7 g (0.20 mol) of potassium and 21.5 g (0.20 mol) of thiophenol in 450 ml of ethanol, at 0°. The reaction mixture was stirred overnight at room temperature and then poured on H₂O and extracted with ether. The combined extracts were washed with 10% aqueous NaOH, aqueous NH₄Cl, aqueous NaHCO₃ and aqueous NaCl. After drying over Na₂SO₄ and evaporating the solvent at reduced pressure, the product was distilled on a 10 cm Vigreux column to provide 16.5 g of (−)-(1R,6S)-2,2,6-trimethyl-1-(phenylthiomethyl)-cyclohexane.

B. p. 117–119°/0.9×10² Pa; yield 64%; $[α]^D_{20}$=−11.1°; IR: 3010, 2900, 1580, 1475, 1360, 1167, 1018, 945, 725 cm⁻¹; NMR(¹H, 360 MHz, CDCl₃): 0.88(s, 3H); 0.93(s, 3H); 1.01(d, J=7.7 Hz, 3H); 0.96–1.08(m, 1H); 1.19(m, 1H); 1.32–1.61(m, 5H); 1.67(m, 1H); 2.76(dd, J=5.4, 11.0 Hz, 1H); 3.01(dd, J=3.5, 11.0 Hz, 1H); 7.16(m, 1H); 7.29(m, 4H) δ ppm. MS: 240(29, M⁺), 138(10), 123(55), 109(100), 95(35), 83(33), 69(43), 55(26), 41(30).

28 g (0.16 mol) of MCPBA (m-chloroperoxybenzoic acid) were slowly added to a solution of 16.5 g (66.5 mmol) of the thioether prepared above in 250 ml of CH₂Cl₂, at 0°. The ice bath was removed and the mixture was left overnight under stirring. The reaction was quenched with H₂O and the mixture was extracted with ether. The organic layer was washed twice with aqueous NaHCO₃ and once with aqueous NaCl. The reaction product was dried over Na₂SO₄ and concentrated to give a viscous oil. The latter crystallized when left at rest to yield 18.5 g (yield 99%) of phenyl (2,2,6-trimethyl-1-cyclohexyl)methyl sulfone. This product was recrystallized 3 times in ethanol to provide a single pure enantiomer, i.e. (+)-(1R,6S).

M. p. 73°; $[α]^D_{25}$=+23.71° (toluene, c=39.308 g/100 ml); IR: 3112,2900, 1580, 1440, 1295, 1168, 1143, 975, 760 cm⁻¹; NMR(¹H, 360 MHz, CDCl₃): 0.72(s, 3H); 0.83(s, 3H); 0.94(d, J=7 Hz, 3H); 1.02(m, 1H); 1.52–1.99(m, 5H); 1.61(m, 1H); 1.70(m, 1H); 2.94(dd, J=4, 15 Hz, 1H); 3.11 (dd, J=3.5, 15 Hz, 1H); 7.56(t, J=7 Hz, 2H); 7.64(t, J=7 Hz, 1H); 7.93(d, J=7 Hz, 1H) δ ppm. MS: 280(1, M⁺), 169(3), 138(83), 123(48), 109(10), 95(39), 83(52), 77(100), 69(42), 55(43), 51(18), 41(39).

b) (−)-(2S)-2-propyloxirane

In a flask, 48.5 g (0.41 mol) of D-norvaline were dissolved in 700 ml of HCl (6N) and the solution was cooled to −8°. Under vigorous stirring, 46.4 g (0.67 mol) of NaNO₂ were added thereto, while maintaining the reaction temperature between −8° and −5°. After stirring for 15 h at −5°, the reaction mixture was extracted with ether. The combined extracts were washed with an aqueous solution saturated in NaCl, then dried on Na₂SO₄ and concentrated. The raw product thus obtained, 48.1 g, was dissolved in 50 ml of ether and added dropwise to a suspension of 12.5 g (0.33 mol) of LiAlH₄ in 200 ml of ether, at −10°. The excess of LiAlH₄ was hydrolized with 30 ml of water and 250 ml of 10% aqueous H₂SO₄ were added thereto in order to dissolve the resulting aluminum salts. The organic phase was separated, the aqueous phase was saturated with NaCl and extracted twice with ether. The combined organic extracts were dried over Na₂SO₄ and concentrated at atmospheric pressure. After distillation on a 15 cm Vigreux column, 27.3 g of 2-chloro-1-pentanol were obtained (M. p. 66–69°; yield 53%).

To a solution of 26.0 g (0.21 mol) of the chloropentanol thus obtained and 33 g (0.42 mol) of pyridine in 500 ml of toluene, at 0°, were added, portionwise, 57.5 g (0.25 mol) of 3,5-dinitrobenzoyl chloride. After stirring overnight, the mixture was poured on H₂O and extracted with toluene. The combined extracts were washed with 10% aqueous HCl and aqueous solutions saturated in NaHCO₃ and NaCl. The product was dried on Na₂SO₄ and concentrated at reduced pressure. The raw chlorodinitrobenzoate thus formed was recrystallized 5 times from a 2:1 isopropyl ether/ethanol mixture to provide 26 g of pure product [a single enantiomer with (2R) configuration]. To a mixture of 24.0 g (75.8 ml) of this product and 250 ml of methanol was added 1 ml of 30%

CH₃ONa in methanol. After 1 h, the rose solution was poured on saturated aqueous NaCl and extracted 3 times with ether. The extracts were washed with saturated NaCl, dried ($Na_2SO_4$) and concentrated at atmospheric pressure. After distillation, 8.1 g of (2R)-2-chloro-1-pentanol were obtained, 6.94 g (56.6 mol) of which were cooled to 0°. 6.4 g (0.11 mol) of freshly ground KOH were then added. The mixture was stirred for 1 h at room temperature and distilled in a bulb-to-bulb apparatus (atmospheric pressure). Further distillation on $CaH_2$ provided 4.7 g of (−)-(2S)-2-propyloxirane (yield. 96% from chloropentanol).

B. p. 90° (bath); $[\alpha]^P{}_{25}=-15.8°$; IR: 2925, 1455, 1403, 1378, 1255, 1130 (broad) $cm^{-1}$; NMR($^1H$, 360 MHz, $CDCl_3$): 0.98(m, 3H); 1.51(m, 4H); 2.47(dd, J=3.5 Hz, $^1H$); 2.75(t, J=3 Hz, 1H); 2.91(m, 1H) δ ppm. MS: 86(0, M⁺), 71(71), 55(15), 43(16), 41(100), 39(32).

c) (1'R,3S,6'S)-1-phenylsulfonyl-1-(2',2',6'-trimethyl-1'-cyclohexyl)-3-hexanol 4.8 g (17.1 mmol) of the sulfone obtained in a) were dissolved in 150 ml of THF, the solution was cooled to −30° and 11 ml of n-butyl-lithium (1.68N) were added dropwise. The reaction temperature was kept between −30° and −40° for 2.5 h and then lowered to −78°. 2.0 g (20.8 mmol) of (−)-(2S)-2-propyloxirane prepared according to b), in 17 ml of HMPA (hexamethylphosphoramide) were added to the reaction mixture and then, dropwise, 3.0 ml of $BF_3$—$(C_2H_5)_2O$. After stirring for 5 h at −78°, the mixture was allowed to warm up to room temperature overnight. The reaction mixture was poured on $H_2O$ and extracted with ether. The extract was washed with an aqueous solution saturated with $NaHCO_3$ and with an aqueous solution saturated with NaCl. After drying over $Na_2SO_4$ and concentrating at reduced pressure, the product was chromatographed on a silica gel column, using toluene, a 2% mixture or ethyl acetate/toluene and a 4% mixture of ethyl acetate/toluene as eluting agent, to yield the desired hydroxy-sulfone in the form of a mixture of diastereomers [yield 65% from the sulfone prepared in a)].

IR: 3450, 2920, 1455, 1443, 1290, 1135, 1180 $cm^{-1}$; NMR($^1H$, 360 MHz, $CDCl_3$: (mixture of two diastereomers): 0.33(s); 0.73(s); 3.26(d, J=7 Hz); 3.61(m); 3.74(m, absent with $D_2O$); 7.50–7.68(m); 7.92(dd, J=7.16 Hz) δ ppm. MS: 366(0, M⁺), 225(20), 207(21), 137(32), 123(39), 109(39), 95(41), 81(49), 77(25), 73(51), 69(93), 55(100), 41(87).

d) 3.7 g (10 mmol) of the hydroxy-sulfone prepared in c) were dissolved in 100 ml of THF and the solution was cooled to −78°. Lithium naphthalide (0.7 M/THF) was added dropwise until a persistent green color was obtained (40 ml). After 10 min., 20 ml of ethanol were added and the temperature was allowed to increase up to room temperature. The reaction mixture was poured on $H_2O$ and extracted with hexane. The extracts were washed with a 10% NaOH aqueous solution, a 10% HCl aqueous solution and an aqueous solution saturated in NaCl. The product was dried over $Na_2SO_4$ and concentrated. This raw product was filtered to eliminate naphthalene ($SiO_2$, 50 g; eluting agent: hexane, then ether) and then bulb-to-bulb distilled (190°/0.5×10² Pa) to provide 1.6 g of a raw mixture containing the desired alcohol together with its unsaturated chain homologue, in the proportion of 5.5:1.

This raw mixture was treated with 10 ml of acetic anhydride (11 g; 0.11 mol), 3 ml of triethylamine (2.1 g; 0.02 mol) and 50 mg of dimethylaminopyridine for 1 h, at a temperature between 0 and 5°. After pouring on water and extracting with hexane, the extracts were washed with water, $NaHCO_3$ and NaCl, dried over $Na_2SO_4$ and concentrated. The residue was dissolved in 25 ml of hexane, cooled to −78° and saturated with ozone until the blue color persisted for 30 min. The solution was degassed with nitrogen, warmed to 0° and added, over a period of 10 min., to a slurry of 1.0 g (26 mmol) of $LiAlH_4$ in 20 ml of ether. The temperature was allowed to increase to reflux and the stirring was continued for 1 h. After hydrolyzing with 5 ml of 3% NaOH, filtering the white precipitate, separating the aqueous phase and concentrating, 0.85 g of the desired hexanol were obtained, without any trace of its saturated chain homologue. This product was carefully purified on a silica column of the Merck "Lobar C" type, using as eluting agent a mixture of 39:1 hexane/ethyl acetate. The purest fractions were selected and distilled in a bulb-to-bulb apparatus (200°/0.5×10² Pa) to yield 0.41 g (yield 18% from the hydroxy-sulfone) of (+)-(1'R,3S,6'S)-1-(2',2',6'-trimethyl-1'-cyclohexyl)-3-hexanol above 99% pure. The analytical data for this compound were the following:

$[\alpha]^P{}_{20}=+12.6°$ (ethanol, c=10.0 g/100 ml); IR: 3310, 2860, 1450, 1362, 994 $cm^{-1}$; NMR($^1H$, 360 MHz, $CDCl_3$): 0.50(m, 1H); 0.79(s, 3H); 0.89(s, 3H); 0.89(d, J=6.8 Hz, 3H); 0.93(t, J=6.5 Hz, 3H); 1.00–1.20(m, 2H); 1.20–1.70(m, 14H); 3.55(broad s, 1H) δ ppm. MS: 226(0, M⁺), 208(15), 193(28), 183(12), 165(12), 152(11), 138(28), 124(45), 109 (57), 95(43), 82(45), 69(68), 55(100), 41(88).

EXAMPLE 4

Preparation of (+)-(1'R,3R,6'S)-1-(2',2',6'-trimethyl-1'-cyclohexyl)-3-hexanol a) (+)-(2R)-2-propyloxirane This compound was prepared as described in Example 3b), but starting from L-norvaline. Its analytical data were identical to those of its antipode, with the exception of $[\alpha]^P{}_{25}=+16.0°$ b) (1'R,3R,6'S)-1-phenylsulfonyl-1-(2',2',6'-trimethyl-1'-cyclohexyl)-3-hexanol This hydroxy-sulfone was prepared according to the method described in Example 3c), starting from the sulfone obtained in Example 3a) and from (+)-(2R)-2-propyloxirane prepared as descrived above. 5.0 g (17.8 mmol) of (+)-(1R, 6S) phenyl (2,2,6-trimethyl-1-cyclohexyl) methyl sulfone, 3.4 g (39.5 mmol) of (+)-(2R)-2-propyloxirane, 12 ml of n-butyllithium (1.68N) and 4.5 ml of $BF_3$—$(C_2H_5)_2O$ were used. (1'R,3R,6'S)-1-phenylsulfonyl-1-(2',2',6'-trimethyl-1'-cyclohexyl)-3-hexanol (mixture of two diastereomers) was obtained in 61% yield calculated on the starting sulfone.

IR: 3500, 2925, 1450, 1295, 1143, 1023 $cm^{-1}$; NMR($^1H$, 360 MHz, $CDCl_3$): 0.78(s); 0.86(s); 1.03(d, J=7 Hz); 3.46 (m); 3.65–3.80(m); 4.01(d, J=8 Hz); 7.15–7.28(m); 7.50–7.66(m); 7.91(d, J=7 Hz) δ ppm. MS: 366(0, M⁺), 225(9), 207(12), 137(19), 123(24), 109(23), 95(31), 81(35), 73(31), 69(69), 55(100), 41(93).

c) The process of Example 3d) was followed, using as starting product the hydroxy-sulfone obtained in b). 700 mg (yield 29% from the hydroxy-sulfone) of (+)-(1'R,3R,6'S)-1-(2',2',6'-trimethyl-1'-cydohexyl)-3-hexanol, more than 99% pure, were obtained.

$[\alpha]^P{}_{20}=+12.1°$ (ethanol, c=10.0 g/100 ml); IR: 3310, 2860, 1450, 1362, 1120, 998 $cm^{-1}$; NMR($^1H$, 360 MHz, $CDCl_3$): 0.50(m, 1H); 0.79(s, 3H); 0.89(s, 3H); 0.89(d, J=6.5 Hz, 3H); 0.95(t, J=7.2 Hz, 3H); 1.10–1.30(m, 2H); 1.30–1.70(m, 14H); 3.65(broad s, 1H) δ ppm. MS: 226(0, M⁺), 208(13), 193(23), 183(13), 165(11), 152(10), 138(26), 123(43), 109(52), 95(44), 82(40), 69(73), 55(100), 41(85).

EXAMPLE 5

Preparation of (−)-(1'S,3S,6'R)-1-(2',2',6'-trimethyl-1'-cyclohexyl)-3-hexanol a) (−)-(1S,6R) phenyl (2,2,6-trimethyl-1-cyclohexyl)methyl sulfone This sulfone was prepared according to a method analogous to that described in Example 3a) but starting from (−)-(1S,6R)-2,2,6-trimethyl-1-cyclohexanecarbaldehyde ($[\alpha]^D_{25}$=−0.80°; 1S:1R=9:1 mixture; prepared according to the process described in U.S. Pat. No. 4,800,233). (+)-(1S,6R)-2,2,6-Trimethyl-1-(phenylthiomethyl)-cydohexane was obtained in 62% yield, presenting the following analytical data:

B. p. 110–111°/0.65×10² Pa; $[\alpha]^D_{25}$=+12.4°.

All other data were identical to those of the antipode described in Example 3a).

This thioether was then converted as previously described to provide, in 99% yield, the above-mentioned sulfone. The latter was recrystallized 5 times from ethanol to provide a single pure enantiomer, i.e. (−)-(1S,6R) phenyl (2,2,6-trimethyl-2-cyclohexyl)methyl sulfone.

M. p. 79.5°; $[\alpha]^D_{25}$=−24.55° (toluene, c=35.028 g/100 ml).

The remainder of the analytical data were identical to those described for its antipode in Example 3a).

b) (1'S,3S,6'R)-1-phenylsulfonyl-(2',2',6'-trimethyl-1'-cyclohexyl)-3-hexanol

Obtained in 66% yield from the sulfone described under a) and (−)-(2S)-2-propyloxirane [Example 3b)], according to the process described in Example 3c).

5.0 g (17.8 mmol) of (−)-(1S,6R) phenyl (2,2,6-trimethyl-1-cyclohexyl) methyl sulfone, 2.3 g (26.7 mmol) of (−)-(2S)-2-propyloxirane, 12 ml of n-butyllithium (1.68N) and 3.2 ml of $BF_3$—$(C_2H_5)_2O$ were used. The desired above-mentioned hydroxy-sulfone was obtained in the form of a mixture of two diastereomers.

IR: 3400 (broad), 2910, 1458, 1445, 1380, 1292,1135, 1075, 1015 cm⁻¹; NMR(¹H, 360 MHz, CDCl₃): 0.78(s); 0.86(s); 1.03(d, J=7 Hz); 3.46(m); 3.65–3.80(m); 4.10(d, J=8 Hz); 7.13–7.28(m); 7.50–7.66(m); 7.91(d, J=7 Hz) δ ppm. MS: 366(0, M⁺), 225(9), 207(11), 137(19), 123(23), 109 (23), 95(33), 81(36), 73(31), 69(70), 55(100), 41(98).

c) The process described in Example 3d) was followed using as a starting product the hydroxy-sulfone prepared in b). 450 mg (yield 21% from the hydroxy-sulfone) of (−)-(1'S,3S,6'R)-1-(2',2',6'-trimethyl-1'-cyclohexyl)-3-hexanol, more than 99% pure, were obtained.

$[\alpha]^D_{20}$=−11.6° (ethanol, c=10.1 g/100 ml)

Other analytical data for this compound were identical to those of its isomer which is the object of Example 4.

EXAMPLE 6

Preparation of (−)-(1'S,3R,6'R)-1-(240 ,2',6'-trimethyl-1'-cyclohexyl)-3-hexanol a) (1'S,3R,6'R)-1-phenylsulfonyl-(2',2',6'-trimethyl-1'-cyclohexyl)-3-hexanol This hydroxy-sulfone was prepared according to the method described in Example 3c), starting from the sulfone obtained in Example 5a) and (+)-(2R)-2-propyloxirane obtained according to Example 4a).

5.0 g (17.8 mmol) of (−)-(1S,6R) phenyl (2,2,6-trimethyl-1-cyclohexyl) methyl sulfone, 3.4 g (39.5 mmol) of (+)-(2R)-2-propyloxirane, 12 ml of n-butyllithium (1.68N) and 4.5 ml of $BF_3$—$(C_2H_5)_2O$ were used.

(1'S,3R,6'R)-1-Phenylsulfonyl-(2',2',6'-trimethyl-1'-cyclohexyl)-3-hexanol (mixture of 2 diastereomers) was obtained in 74% yield calculated from the starting sulfone.

IR: 3450 (broad), 2940, 1460, 1445, 1300, 1140, 1080 cm⁻¹; NMR(¹H, 360 MHz, CDCl₃): 0.33(s); 0.73(s); 3.28(d, J=7 Hz); 3.62(m); 7.13–7.29(m); 7.50–7.68(m); 7.91(dd, J=7.16 Hz) δ ppm. MS: 366(0, M⁺), 225(7), 207(9), 137(16), 123(20), 109(20), 81(34), 73(33), 69(69), 55(100), 41(97).

b) The process of Example 3d) was followed, starting from the hydroxy-sulfone prepared according to a). 410 mg (yield 14% starting from the hydroxy-sulfone) of (−)-(1'S,3R,6'R)-1-(2',2',6'-trimethyl-1'-cydohexyl)-3-hexanol, more than 99% pure, were obtained.

$[\alpha]^D_{20}$=−11,1° (ethanol, c=9,9 g/100 ml)

Other analytical data for this compound were identical to those or its enantiomer described in Example 3.

EXAMPLE 7

Preparation of (+)-(1'R,6'S)-5-methyl-1-(2',2',6'-trimethyl-1'-cyclohexyl)-3-hexanol This compound was prepared according to the method described in Example 1, starting from (+)-(1R,6S)-2,2,6-trimethyl-1-cyclohexanecarbaldehyde (5 g, 32 mmol; obtained according to the method described in U.S. Pat. No. 4,800,233), 20 ml of ethanol, 0.92 g (0.04 at. g) of Na cut in squares and 5 g (50 mmole) of 4-methyl-2-pentanone. After the treatment previously described and bulb-to-bulb distillation (150°/13.3 Pa) 4.94 g (yield 65%) of product, containing (+)-(1'R,6'S)-5-methyl-1-(2',2',6'-trimethyl-1'-cyclohexyl)-1-hexen-3-one, in admixture with its isomer (1'S,6'S) in a ratio 92:8, were obtained.

$[\alpha]^D_{20}$=+16.1°; IR: 1700, 1675, 1625, 1000 cm⁻¹; NMR (¹H, 360 MHz): 0.75(d, J=6.5 Hz, 3H); 0.82 and 0.895(2s, 2×3H); 0.95(d, J=7.2 Hz, 6H); 2.16(m, 1H); 2.415(d, J=7.2 Hz, 2H); 6.48(d, J=15 Hz, 1H); 5.72(dxd, J=10 Hz et 15 Hz, 1H) δ ppm. MS: 236(8, M⁺), 221(8), 193(24), 179(32), 161(15), 151(45), 136(52), 124(26), 109(60), 95(100), 85(68), 81(58), 69(58), 55(70), 41(58).

3 g of this mixture were then hydrogenated in 30 ml of ethanol and in the presence of 0.3 g of Raney nickel (room temperature and atmospheric pressure). After filtration and distillation in a bulb-to-bulb apparatus (150°/13.3 Pa), 2.7 g of a mixture containing (+)-(1'R,6'S)-5-methyl-1-(2',2',6'-trimethyl-1'-cyclohexyl)-3-hexanone (92%) and 8% of its isomer (1'S,6'S) (yield 93%) were obtained.

$[\alpha]^D_{20}$=+6.6°; IR: 1715 cm⁻¹ (C=0); NMR(¹H, 360 MHz): 0.54(ddd, J=2.4 Hz, 5.2 Hz, 11 Hz, 1H); 0.8 and 0.874(2s, 2×3H); 0.78(d, J=6.5 Hz, 3H); 0.91(d, J=7.2 Hz, 6H); 2.13(m, 1H); 2.26(d, J=7.2 Hz, 2H); 2.3–2.53(m, 2H) δ ppm. MS: 238(12, M⁺), 223(4), 205(4), 195(2), 181(22), 163(22), 153(7), 138(45), 123(30), 100(16), 95(40), 85(68), 69(70), 57(100), 41(46).

This mixture was then reduced as described in Example 1b), using 0.19 g (5 mmol) of $LiAlH_4$ in suspension in 15 ml of dry ether and 23 g (9.7 mmol) of ketone in 10 ml of ether. The reaction mixture was left at reflux for 2 h and then treated with 0.19 ml of $H_2O$, 0.19 ml of NaOH (15%) and 0.57 ml of $H_2O$. The product was filtered, concentrated and distilled in a bulb-to-bulb apparatus (150°/13.3 Pa) to yield 2.15 g of pure product containing 92% of (+)-(1'R,6'S)-5-methyl-1-(2',2',6'-trimethyl-1'-cyclohexyl)-3-hexanol and 8% of its isomer (1'S,6'S).

$[\alpha]^D_{20}$=+8.7°; IR: 3350 cm⁻¹; NMR(¹H, 360 MHz): 0.526(m, 1H); 0.795 et 0.89(2s, 2×3H); 0.85–0.95(m, 3×3H); 3.61(m, 1H) δ ppm. MS: 240(2, M⁺), 222(4), 207(8), 183(5), 166(3), 151(2), 138(18), 123(28), 109(42), 95(40), 83(38), 69(100), 55(45), 41(40).

EXAMPLE 8

Preparation of (−)-(1'S,6'R)-5-methyl-1-(2',2',6'-trimethyl-1'-cyclohexyl)-3-hexanol This compound was prepared exactly in the same manner as that described in Example 7, but starting from (−)-(1S, 6R)-2,2,6-trimethyl-1-cyclohexanecarbaldehyde.

The products obtained presented the same analytical data as their isomers described in Example 7, with the following exceptions:

(−)-(1'S,6'R)-5-methyl-1-(2',2',6'-trimethyl-1'-cyclohexyl)-1-hexen-3-one
[in admixture with 8% (1'R,6'R), 2.62 g, yield 35%]
$[\alpha]^D_{20} = -14.8°$ (−)-(1'S,6'R)-5-methyl-1-(2',2',6'-trimethyl-1'-cyclohexyl)-3-hexanone
[in admixture with 8% (1'R,6'R), 2.8 g, yield 95%]
$[\alpha]^D_{20} = -6.3°$ (−)-(1'S,6'R)-5-methyl-1-(2',2',6'-trimethyl-1'-cyclohexyl)-3-hexanol
[in admixture with 8% (1'R,6'R), 2.1 g, yield 92%]
$[\alpha]^D_{20} = -8.3°$

EXAMPLE 9

Preparation of a Perfuming Composition

A base perfuming composition of the floral, musky, aromatic type was prepared by admixing the following ingredients (parts by weight):

| Ingredients | Parts by weight |
|---|---|
| Iralia ®[1] | 120 |
| Cyclosia ®[2] base | 100 |
| 10%* Exaltolide ®[3] | 100 |
| Musk ketone | 80 |
| Musk xylol | 70 |
| Musk ambrette | 60 |
| Coumarine | 60 |
| Rosinol cryst. | 50 |
| Patchouli essential oil | 50 |
| Eugenol | 45 |
| Resinoid galbanum essential oil | 35 |
| White rose essential oil | 30 |
| Lilial ®[4] | 30 |
| Vetyveryl acetate | 30 |
| Methyleugenol | 20 |
| Tricyclone[5] | 20 |
| β-ionone | 10 |
| Synthetic jasmin | 10 |
| Benzoin resin essential oil | 10 |
| Terpeneless orange essential oil | 10 |
| Total | 940 |

*in dipropyleneglycol (DIPG)
[1] methylionone; origin: Firmenich SA, Geneva, Switzerland
[2] hydroxycitronellal; origin: Firmenich SA, Geneva, Switzerland
[3] cyclopentadecanolide; origin: Firmenich SA, Geneva, Switzerland
[4] 3-(4-tert-butyl-1-phenyl)-2-methylpropanal; origine: L. Givaudan, Vernier, Switzerland
[5] 10,10-dimethyl-cis-tricyclo[7.1.1.0$^{2,7}$]undec-2-en-4-one (mixture of isomers); origin: Firmenich SA, Geneva, Switzerland With this base composition, five compositions A, B, C, D and E were prepared containing the following ingredients:

| Ingredients | A | B | C | D | E |
|---|---|---|---|---|---|
| Base composition | 940 | 940 | 940 | 940 | 940 |
| 10%* trans-1-(2,2,6-trimethyl-1-cyclohexyl)-3-hexanol [racemic mixture] | 60 | — | — | — | — |
| 10%* (+)-(1'R,6'S)-1-(2',2',6'-trimethyl-1'-cyclohexyl)-3-hexanol [mixture of C(3) epimers] | — | 60 | — | — | — |
| (−)-(1'S,6'R)-1-(2',2',6'-trimethyl-1'-cyclohexyl)-3-hexanol [mixture of C(3) epimers] | — | — | 60 | — | — |
| 10%* (+)-(1'R,3S,6'S)-1-(2',2',6'-trimethyl-1'-cyclohexyl)-3-hexanol | — | — | — | 60 | — |
| 1%* (+)-(1'R,3'S,6'S)-1-(2',2',3',6'-tetramethyl-1'-cyclohexyl)-3-hexanol | — | — | — | — | 60 |
| Total | 1000 | 1000 | 1000 | 1000 | 1000 |

*in dipropyleneglycol (DIPG)

The five compositions thus obtained were comparatively evaluated by a panel of expert perfumers. According to the latter, when compositions A, B and C were compared to the base composition, it was found that the odor of this base composition had become richer in a very elegant and warm woody note, increasingly marked and powerful in novel composition B than in composition A, the woody note of composition C being weaker, in spite of the fact that the amount it contained of its respective perfuming ingredient according to the invention was ten times higher than the amount of the other two perfuming ingredients added to compositions A and B. In addition, it was the perfumers' opinion that, amongst the three, novel composition B was clearly preferred, for its odor was not only more powerful, but it also possessed a neater woody character. This character was found to be further reinforced in composition D, when the latter was compared to composition B.

Furthermore, when compositions D and E, containing the two preferred compounds of the invention, were evaluated for comparison, all the perfumers agreed that composition E developed a woody odor stronger than that of composition D, even if the latter contained (+)-(1'R,3S, 6'S)-1-(2',2',6'-trimethyl-1'-cyclohexyl)-3-hexanol in a concentration ten times higher than the content of composition E in (+)-(1'R, 3'S,6'S)-1-(2',2',3',6'-tetramethyl-1'-cyclohexyl)-3-hexanol. This result clearly showed the superior olfactive strength of the latter perfuming ingredient, but composition E was not unanimously preferred, nonetheless. In fact, several perfumers preferred the rounder and more elegant woody character of composition D, while others appreciated better the drier and more animal woody note of composition E. These results showed that the two perfuming ingredients according to the invention could be used and were appropriate for quite distinct perfumery applications, since the odor properties of one compound did not emulate those of any other.

EXAMPLE 10

Preparation of a Perfuming Composition Intended for a Masculin Type Perfume

A base perfuming composition was prepared by admixing the following ingredients (parts by weight):

| Ingredients | Parts by weight |
|---|---|
| 10%* Carbinol acetate | 200 |
| Geranyl acetate | 50 |
| Linalyl acetate | 1200 |
| Muscone | 100 |
| 10%* Raspberry ketone | 30 |
| Bergamot essential oil | 300 |
| Synthetic bergamot | 300 |

-continued

| Ingredients | Parts by weight |
|---|---|
| Citral pure | 120 |
| Lemon essential oil | 1500 |
| Galaxolide ®[1)] 50 | 250 |
| Exaltex ®[2)] | 100 |
| Clove bud essential oil | 300 |
| Lavander essential oil | 600 |
| Linalol | 200 |
| Lyral ®[3)] | 1000 |
| Sweet marjoram essential oil | 350 |
| 50%* Oakmoss absolute | 150 |
| Nutmeg essential oil | 500 |
| Benzyl salicylate | 50 |
| Sandela ®[4)] | 600 |
| Ylang | 300 |
| 10%* Galbanum essential oil | 300 |
| Total | 8500 |

*in dipropyleneglycol (DIPG)
[1)]1,3,4,6,7,8-hexahydro-4,6,6,7,8,8-hexamethylcyclopenta [g] isochromene; origin: IFF Inc., USA
[2)]cyclopentadecanolide; origin: Firmenich SA, Geneva, Switzerland
[3)]4-(4-hydroxy-4-methylpentyl)-3-cyclohexene-1-carboxaldehyde; origine: IFF Inc., USA
[4)]3-(isocamphyl-5)-cyclohexan-1-ol; origine: L. Givaudan, Vernier, Switzerland.

Four perfuming compositions A, B, C and D were prepared by admixing, into this citrus, spicy, floral, green type base composition, respectively 1500 parts by weight of 1%* racemic 1-(2,2,c-3,t-6-tetramethyl-r-1-cyclohexyl)-3-hexanol (composition A), 1500 parts by weight of 1%* (+)-(1'R,3'S,6'S)-1-(2',2',3',6'-tetramethyl-1'-cyclohexyl)-3-hexanol (composition B), 1500 parts by weight of 1%* (−)-(1'S,3'R,6'R)-1-(2',2',3',6'-tetramethyl-1'-cyclohexyl)-3-hexanol (composition C) and 1500 parts by weight of 10%* (+)-(1'R,3S,6'S)-1-(2',2',6'-trimethyl-1'-cyclohexyl)-3-hexanol (composition D).

A panel of expert perfumers, evaluating these four compositions, found that, when compared to the base composition, new composition B possessed a woody-amber connotation, dry and very perceptible, while composition C was entirely devoid of any woody character. Furthermore, when compared with composition A, the woody-amber character of composition B was much more pronounced, composition A having also a weaker woody note. In addition, it was the perfumers' opinion that the woody note of composition D was rounder and less dry than that of composition B, the latter developing a more animal odor.

EXAMPLE 11

Preparation of a Perfuming Composition Intended for a Masculine Type Perfume

A base perfuming composition was prepared by admixing the following ingredients (parts by weight):

| Ingredients | Parts by weight |
|---|---|
| Linalyl acetate | 480 |
| Bergamot essential oil | 200 |
| Citral pure | 20 |
| Lemon esssential oil | 50 |
| 50%* Purif.civet | 30 |
| Coumarine | 80 |
| China geranium ess. oil | 30 |

-continued

| Ingredients | Parts by weight |
|---|---|
| Hedione ®[1)] | 750 |
| Lavandin | 180 |
| Levo-citronellol | 90 |
| Linalol | 30 |
| Lyral ®[2)] | 310 |
| Mandarin essential oil | 60 |
| 5%* Oakmoss absolute | 40 |
| Patchouli essential oil | 720 |
| Polysantol ®[3)] | 20 |
| Clary sage essential oil | 30 |
| Vanillin | 20 |
| Vertofix coeur[4)] | 410 |
| Total | 3550 |

*in dipropyleneglycol (DIPG)
[1)]methyl dihydrojasmonate; origin: Firmenich SA, Geneva, Switzerland
[2)]see Example 10
[3)](1R',E)-3,3-dimethyl-5-(2',2',3'-trimethyl-3'-cyclopenten-1'-yl)-4-penten-2-ol; origin: Firmenich SA, Geneva, Switzerland
[4)]origin: IFF Inc., USA To this base composition, which already possessed a very woody character, there were added respectively 50 parts by weight of racemic trans-1-(2,2,6-trimethyl-1-cyclohexyl)-3-hexanol to prepare a composition A, 50 parts by weight of (+)-(1'R,6'S)-1-(2',2',6'-trimethyl-1'-cyclohexyl)-3-hexanol to prepare a novel composition B and 50 parts by weight of (+)-(1'R,3S,6'S)-1-(2',2',6'-trimethyl-1'-cyclohexyl)-3-hexanol to prepare a novel composition C The two compositions A and B were then evaluated on a blind test by a panel of five expert perfumers who unanimously preferred composition B. The latter was judged to possess a much more powerful odor, with a remarkably enhanced woody-amber-cedar character, the woody note of which was also judged much more elegant and pronounced than that of composition A. The olfactive character of the two compositions was also judged to be distinct.

In addition, when asked to further evaluate composition C, still on a blind test, the perfumers were of the opinion that the latter possessed an olfactive character similar to that of composition B but clearly enhanced and even more elegant and warm-woody. Composition C now possessed an almost overpowering woody and dry character, which was not judged identical to that of composition B and which, in their opinion, was distinct from the odor effect that would have been expected if composition C contained just a higher concentration of the same active ingredient present in composition B.

In a further blind test, the perfumers were asked to indicate their preference between a composition prepared identically to composition A above and a novel composition D prepared by adding to the base perfuming composition 25 parts by weight of (+)-(1'R,6'S)-1-(2',2',6'-trimethyl-1'-cyclohexyl)-3-hexanol. Without hesitation, all the perfumers indicated their preference for composition D which not only possessed a more powerful odor, but also had a markedly more elegant character. In their opinion, there was no doubt that, given the choice, they would prefer to use composition D to achieve an olfactive effect of the woody-amber-cedar type.

EXAMPLES 12–23

Perfuming of Various Consumer Articles

The articles mentioned below were perfumed by means of (+)-(1'R,6'S)-1-(2',2',6'-trimethyl-1'-cyclohexyl)-3-hexanol, which was added to the appropriate non perfumed bases in the concentrations indicated.

| Example | Article | Conc. (% by weight) | Odor/ Aspect [25° C.] | Odor/ Aspect [40° C.] |
|---|---|---|---|---|
| 12 | Cologne (95° alcohol) | 5.0 | S/N | S/N |
| 13 | Cream (O/W) | 0.4 | S/N | S/N |
| 14 | Cream (W/O) | 0.4 | S/N | S/N |
| 15 | Shampoo | 0.5 | S/N | S/N |
| 16 | Talc | 0.5 | S/N | S/N |
| 17 | Antiperspirant roll-on | 0.5 | S/N | S/N |
| 18 | Antiperspirant spray | 0.8 | S/N | S/N |
| 19 | Spray laque | 0.2 | S/N | S/N |
| 20 | Deodorant spray | 1.3 | S/N | S/N |
| 21 | Soap (tallow + coconut oil) | 0.5 | A/N | A/N |
| 22 | Powder detergent | 0.2 | S/N | S/N |
| 23 | Chlorinated household cleaning powder | 0.2 | S/N | S/N |

Key to abbreviations:
S = stable
N = normal
A = acceptable

The table above shows that the compound according to the invention can be widely used in perfumery.

In addition to the stability results above, it was also observed that, where applicable, the odor of the base was perfectly covered by a pleasant and elegant fragrance and that all the products acquired a strong woody, cedar-like odor.

When compared to identical perfuming and stability tests carried out with the prior known corresponding racemate, i.e. trans-1-(2,2,6-trimethyl-1-cyclohexyl)-3-hexanol, it was quite clear that the products perfumed with the compound of the present invention developed a much stronger and woodier odor than those perfumed with the known racemate. In addition, the woody character of the fragrance imparted by the optically active compound of the invention was judged quite distinct from that conferred by the racemate, with a less animal connotation than the latter and a more pronounced woody cedar-like character, whereas the woody note of the racemate was reminiscent of the odor of vetyver oil.

EXAMPLE 24

Comparative Tests on the Woody Character and Strength

On a blind test, a panel of twenty expert perfumers was asked to indicate the preference, as regards the woody character of the note, between two smelling strips A and B, which had been dipped into vials containing 10% solutions in dipropyleneglycol of racemic trans-1-(2,2,6-trimethyl-1-cyclohexyl)-3-hexanol and, respectively, optically active (+)-(1'R,6'S)-1-(2',2',6'-trimethyl-1'-cyclohexyl)-3-hexanol.

Twelve out of the twenty perfumers preferred the woody character of smelling strip B, both as regards the headnote and the bottom note, finding it stronger.

When a similar test was carried out by adding the compounds cited above to a woody-amber type composition, in equal concentrations, all the perfumers judged that the woody character of said composition was far more enhanced by the addition of (+)-(1'R,6'S)-1-(2',2',6')-1-(2',2',6'-trimethyl-1'-cyclohexyl)-3-hexanol than by that of trans-1-(2,2,6-trimethyl-1-cyclohexyl)-3-hexanol. Fourteen out of the twenty preferred the first composition, while the other six appreciated better the composition containing the known racemic compound.

The perfumers also mentioned that, although they could judge on the strength of the woody character, they found it quite difficult to define an absolute preference for one or the other of the compounds tested, since they judged their odor notes to be quite distinct and, depending on the nature of said composition, would use one or the other to achieve different effects.

What we claim is:

1. An optically active compound of formula

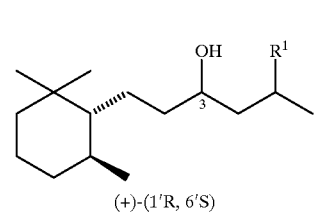

(+)-(1'R, 6'S)

(Ia)

wherein $R^1$ represents a hydrogen atom or a methyl radical, or of formula

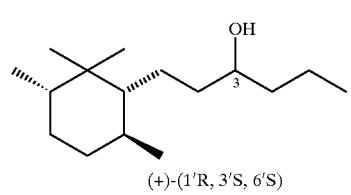

(+)-(1'R, 3'S, 6'S)

(Ic)

2. The compound of claim 1 selected from the group consisting of:
   a) (+)-(1'R,3S,6'S)-1-(2',2',6'-trimethyl-1'-cyclohexyl)-3-hexanol; and
   b) (+)-(1'R,3'S,6'S)-1-(2',2',3',6'-tetramethyl-1'-cyclohexyl)-3-hexanol.

3. A method to confer, improve, enhance or modify the odor properties of a perfuming composition or a perfumed article, which method comprises adding to said composition or article a fragrance effective amount of a compound according to claim 1.

4. A method to confer, improve, enhance or modify the odor properties of a perfuming composition or a perfumed article, which method comprises adding to said composition or article a fragrance effective amount of
   a) (+)-(1'R,3S,6'S)-1-(2',2',6'-trimethyl-1'-cyclohexyl)-3-hexanol or
   b) (+)-(1'R,3'S,6'S)-1-(2',2',3',6'-tetramethyl-1'-cyclohexyl)-3-hexanol.

5. A perfuming composition or a perfumed article containing as an active perfuming ingredient a compound according to claim 1.

6. A perfuming composition or a perfumed article containing as an active perfuming ingredient
   a) (+)-(1'R,3S,6'S)-1-(2',2',6'-trimethyl-1'-cyclohexyl)-3-hexanol or
   b) (+)-(1'R,3'S,6'S)-1-(2',2',3',6'-tetramethyl-1'-cyclohexyl)-3-hexanol.

7. In a method to confer, improve, enhance or modify the odor character of a perfuming composition or a perfumed article, which comprises adding to said composition or article a fragrance effective amount of 1-(2',2',c-3',t-6'- tetramethyl-r-1'-cyclohexyl)-3-hexanol, the improvement therein which consists in adding a preponderant amount of said hexanol in the form of its (+)-(1'R,3'S,6'S) isomer.

8. In a method to confer, improve, enhance or modify the odor character of a perfuming composition or a perfumed article, which comprises adding to said composition or article a fragrance effective amount of trans-1-(2,2,6-trimethyl-1-cyclohexyl)-3-hexanol, the improvement therein which consists in adding a preponderant amount of said hexanol in the form of its (+)-(1'R,3S,6'S) isomer.

9. A method to enhance or improve the woody character imparted to a perfuming composition or to a perfumed article upon addition of a fragrance effective amount of trans-1-(2,2,6-trimethyl-1-cyclohexyl)-3-hexanol, which method comprises adding a preponderant amount of said hexanol in the form of its (+)-(1'R,3S,6'S) isomer.

10. A method to confer, improve, enhance or modify the odor character of a perfuming composition or a perfumed article, which comprises adding to said composition or article a fragrance effective amount of a compound obtained by reacting a hydroxy-sulfone of formula

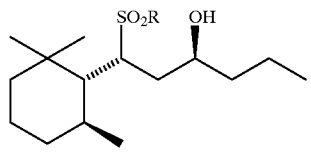

wherein R stands for an alkyl or aryl radical, with an agent capable of the reductive cleavage of the sulfonyl group and subsequently separating said compound from the reaction product.

11. A method according to claim 10 wherein said symbol R in the formula of said hydroxy-sulfone stands for a phenyl radical and said hydroxy-sulfone is reacted with lithium naphthalide.

12. A perfuming composition or a perfumed article resulting from the method according to claim 7.

13. A perfumed article according to claim 5, in the form of a perfume or Cologne, a soap, a bath or shower gel, a shampoo or hair conditioner, a body deodorant, a cosmetic preparation, a detergent or fabric softener, an air freshener or a household product.

14. A perfuming composition or a perfumed article resulting from the method according to claim 8.

15. A perfuming composition or a perfumed article resulting from the method according to claim 9.

16. A perfuming composition or a perfumed article resulting from the method according to claim 10.

17. A perfumed article according to claim 6 in the form of a perfume or Cologne, a soap, a bath or shower gel, a shampoo or hair conditioner, a body deodorant, a cosmetic preparation, a detergent or fabric softener, an air freshener or a household product.

18. (+)-(1'R,3S,6'S)-1-(2',2',6'-trimethyl-1'-cyclohexyl)-3-hexanol having both chemical and optical purity above 99%.

19. (+)-(1'R,3'S,6'S)-1-(2',2',3',6'-tetramethyl-1'-cyclohexyl)-3-hexanol having an optical purity above 98%.

20. The compound of claim 1 in the form of an optically active mixture of C(3) epimers of (+)-(1'R,6'S)-1-(2',2',6'-trimethyl-1'-cyclohexyl)-3-hexanol.

21. The compound of claim 1 in the form of an optically active mixture of C(3) epimers of (+)-(1'R,3'S,6'S)-1-(2',2',3',6'-tetramethyl-1'-cyclohexyl)-3-hexanol.

* * * * *

UNITED STATES PATENT AND TRADEMARK OFFICE
CERTIFICATE OF CORRECTION

Page 1 of 2

PATENT NO. : 6,054,426
DATED : April 25, 2000
INVENTOR(S) : Karl-Heinrick Schulte-Elte, et. al.

It is certified that error appears in the above-identified patent and that said Letters Patent is hereby corrected as shown below:

Column 4, line 20, change "(-)-(1'S,3'r,6')" to --(-)-(1'S,3'R,6'R)--.

Column 5, lines 20 and 21, change "(+)-(1'R,3S,6'S)-1-(2',2',6'-trimethyl-1'-cydohexyl)-3-hexanol" to --(+)-(1'R,3S,6'S)-1-(2',2',6'-trimethyl-1'-cyclohexyl)-3-hexanol--.

Column 7, line 17, change "4-methyl-2pentanone" to --4-methyl-2-pentanone--.

Column 7, after line 20, insert the following line:

--SCHEME I--.

Column 12, line 24, change "($[\alpha]^D_{20}$=+36.00°" to --($[\alpha]^D_{20}$=+36.0°--.

Column 12, line 31, change "(+)-(1R,3S,6S)-2,2,3,6tetramethyl-1-" to --(+)-(1R,3S,6S)-2,2,3,6-tetramethyl-1---.

UNITED STATES PATENT AND TRADEMARK OFFICE
CERTIFICATE OF CORRECTION

PATENT NO. : 6,054,426
DATED : April 25, 2000
INVENTOR(S) : Karl-Heinrick Schulte-Elte, et. al.

It is certified that error appears in the above-identified patent and that said Letters Patent is hereby corrected as shown below:

Column 12, line 49, change "none" to --enone--.

Column 13, line 27, change "none" to --enone--.

Column 13, line 40, change "(+)-(1'R3S6'S)-1-(2',2',6'-trimethyl-" to --(+)-(1'R,3S,6'S)-1-(2',2',6'-trimethyl- --.

Column 15, line 14, change "¹H" to --1H--.

Column 17, line 53, change "(--)-1'S,3R,6'R)-1-(240 ,2',6'-" to --(--)-1'S,3R,6'R)-1-(2',2',6'- --.

Signed and Sealed this

Tenth Day of April, 2001

*Attest:*

NICHOLAS P. GODICI

*Attesting Officer*   *Acting Director of the United States Patent and Trademark Office*